US00PP32387P2

(12) United States Plant Patent
Hansen

(10) Patent No.: US PP32,387 P2
(45) Date of Patent: Oct. 20, 2020

(54) ***SALVIA* PLANT NAMED 'MOULIN ROUGE'**

(50) Latin Name: ***Salvia pratensis* hybrid**
Varietal Denomination: Moulin Rouge

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,095

(22) Filed: Jan. 30, 2020

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./263.1, 475
See application file for complete search history.

*Primary Examiner* — Susan McCormick Ewoldt
*Assistant Examiner* — Karen M Redden

(57) ABSTRACT

The new and distinct cultivar of perennial *Salvia* plant named 'Moulin Rouge' characterized by its large, deep rosy-pink flowers from dark deep-rose buds and calyxes, densely arranged in verticils. The new plant has a medium height, compact, rounded habit with stiff, upright, heavily-branched stems and a strong vigorous growth rate and dark gray-green foliage. 'Moulin Rouge' is useful for landscaping as a specimen plant or en masse.

1 Drawing Sheet

Botanical denomination: *Salvia pratensis* hybrid.
Cultivar designation: 'Moulin Rouge'.

STATEMENT REGARDING PRIOR DISCLOSURES UNDER 37 CFR 1.77(B)(6)

The first public disclosure of the new plant, in the form of a photograph and brief description on a website operated by Walters Gardens, Inc. on Feb. 1, 2019. Subsequently, the new plant was advertised in the "Walters Gardens 19-20 Catalog" first distributed on May 29, 2019. The claimed plant was first sold on May 20, 2019 by Walters Gardens, Inc., who obtained the plant and all information relating thereto, from the inventor. Walters Gardens, Inc. obtained the new plant and all information on the new plant from the inventor. No plants of *Salvia* 'Moulin Rouge' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of ornamental sage plant hereinafter referred to by the cultivar name *Salvia* 'Moulin Rouge' or as the new plant. The new plant was selected from an insect pollination in late spring of 2014 with an unreleased, proprietary hybrid known by the breeder code 13-40-2 (not patented) as the female or seed parent and the male parent is a sibling of 13-40-2 (not patented) at a wholesale perennial nursery in Zeeland, Mich., USA. Seed was collected in the summer of 2014 and sown at the same nursery. The new plant was initially evaluated in the summer of 2016 and assigned the breeder code 14-6-1 through the trial process prior to assigning the cultivar name.

The new *Salvia* was further evaluated and asexually propagated initially by division and later by basal cuttings taken at the same nursery in Zeeland, Mich., USA in 2016. Evaluation of these and further cutting grown plants shows that *Salvia* 'Moulin Rouge' continues to be stable and produce true to type plants in successive generations of asexual propagation.

SUMMARY OF THE INVENTION

Plants of *Salvia* 'Moulin Rouge' have not been observed under all possible environmental conditions. The phenotype may vary somewhat with variations in environment such as temperature, nutrition and light intensity without, however, any variance in genotype.

*Salvia* 'Moulin Rouge' can be closely compared to *Salvia* 'Ballerina Pink' U.S. Plant Pat. No. 29,957, 'Pretty in Pink' U.S. Plant Pat. No. 29,550, 'Pink Dawn' U.S. Plant Pat. No. 26,343, 'Sweet 16' U.S. Plant Pat. No. 24,312, and 'Sweet Petite' U.S. Plant Pat. No. 31,285. 'Ballerina Pink' has soft pink flowers and dark mauve calyces on plants just slightly taller. 'Pretty in Pink' has flowers that are vibrant lavender-pink with darker pink calyxes and slightly taller habit. 'Pink Dawn' has a shorter habit with flowers that are cotton candy pink opening from fuchsia buds. 'Sweet 16' is slightly taller in habit with rose-purple bud opening to lavender pink flowers with a darker purple lower lip. 'Sweet Petite' has significantly shorter habit and flowers of lavender-pink with dark rose buds. Comparison with the male parent is not possible as it was not maintained. The female parent has lighter pink flower and shorter habit.

The following characteristics in combination distinguish *Saliva* 'Moulin Rouge' as a new and distinct cultivar from all other cultivars known to the inventor:

1. Large, deep rosy-pink flowers densely arranged in verticils;
2. Stiff, upright, heavily-branched stems;
3. Dark deep-rose flower buds;

4. Medium to tall height, dense, rounded, strong, vigorous and winter-hardy habit;
5. Rugose, dark, gray-green foliage.

BRIEF DESCRIPTION OF THE DRAWINGS

The photographs of the new plant demonstrate the unique traits and the overall appearance of *Salvia* 'Moulin Rouge'. The colors are as accurate as reasonably possible with color reproductions. Variation in ambient light spectrum, source and direction may cause the appearance of minor variation in color. The plant used in the photographs was a three-year-old plant grown in an open, full-sun trial garden at a wholesale perennial nursery in Zeeland, Mich. with supplemental water and fertilizer when needed.

DETAILED BOTANICAL DESCRIPTION

Figure 1:
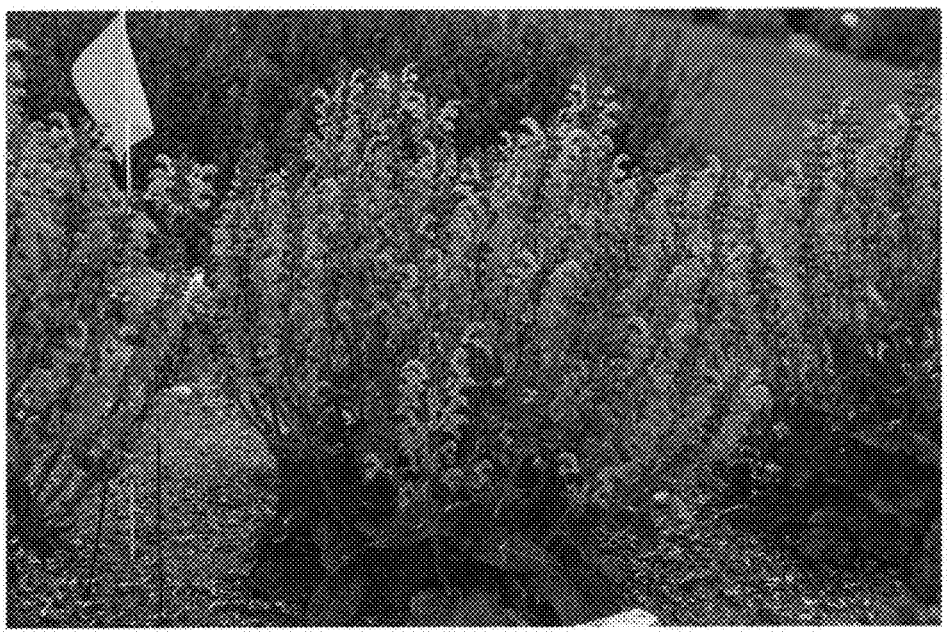
FIG. 1 shows the plant habit in full flower in a landscape.
Figure 2:
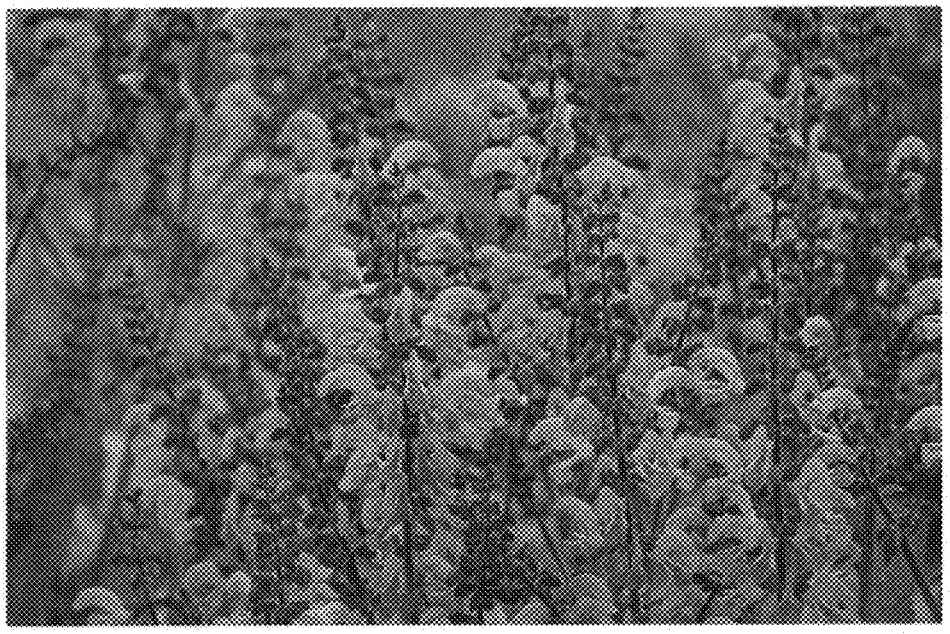
FIG. 2 shows a close-up of the flower scape with the buds, flowers, stems and calyxes.

The following descriptions and color references except where common dictionary terms are used are based on the 2015 edition of The Royal Horticultural Society Colour Chart. *Salvia* 'Moulin Rouge' has not been observed under all possible environments. The phenotype may vary slightly with different growing environments such as temperature, light, fertility, soil pH, moisture and plant maturity levels, but without any change in the genotype. The following observations and size descriptions are based on three-year-old plants growing in an outdoor full-sun trial garden and greenhouse-forced two-year-old plants at a wholesale perennial nursery in Zeeland, Mich. Plants were given supplemental water and fertilizer. Plant growth regulators were used in the greenhouse trials only.

Botanical classification: *Salvia pratensis* hybrid;

Parentage: Female or seed is the proprietary hybrid 13-40-2; male or pollen parent is a sibling to 13-40-2;

Plant habit: Winter-hardy herbaceous perennial; multi-stemmed, compact, rounded, with mostly basal foliage, and flowers in several tightly arranged verticils on branched upright racemes displayed above foliage; in flower with panicles about 60 cm tall and about 64 cm wide at the fullest point; cauline foliage extends up the stems about 32 cm; about 20 flowering panicles per plant;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks.

Root description: Fine, well-branched; color dependent on age and soil type, from cream to dark tan in color;

Foliage: Opposite; simple; slightly rugose; lanceolate; margin irregularly crenate and micro-ciliolate; adaxial sparsely puberulent, and abaxial puberulent; acute apex and base cordate; leaf blades to about 22.5 cm long and 9.5 cm across, decreasing in size distally; average about 19.0 cm long and 6.5 cm across; faint sage fragrance;

Foliage color: Young adaxial between RHS 138A, abaxial between RHS 138A and RHS 138B; mature adaxial nearest NN137A, mature abaxial nearest RHS 147B;

Venation: Reticulate; impressed on adaxial side and costate on abaxial side; micro-puberulent adaxial, abaxial pubescent; nearest RHS 145D; adaxial primary and secondary veins between RHS 146D and RHS 145B; abaxial midrib between RHS 146D and RHS 147C, abaxial primary and secondary veins between RHS 146D and RHS 145C;

Petiole: Concavo-convex; puberulent adaxial and abaxial and ciliolate margin; to about 10.0 cm long and 9.0 mm wide at base decreasing distally, average 7.0 cm long and 7.5 mm wide at base;

Petiole color: Adaxial distal portion nearest RHS 146D slightly blushed with RHS N79B, proximal portion between RHS 146D and RHS 145C moderately blushed with RHS N79B; abaxial distal portion nearest RHS 145C and proximal portion between RHS 146D and RHS 145C moderately blushed with nearest RHS N79B;

Flower description: Perfect; bilabiate; zygomorphic; fused corolla portion glabrous adaxial and puberulent abaxial;

Flower size: 27.0 mm long to tip of exserted stigma, 20.0 mm tall, 7.0 mm wide; corolla 25.0 mm long, 20.0 mm tall; corolla fused basal portion 10.0 mm long, 8.0 mm tall and 5.0 mm wide;

Inflorescence: Panicle; branched at about 45° angle, rarely compound branched; branches to 32 cm long and 3.0 mm across base; flowering portion 28 cm tall and 38 cm across; verticillate with flowering generally beginning at lower verticils and advancing up the scape, but not all flowers at each verticil opening at the same time giving the effect of a scape being in continuous flower for longer periods; typically six flowers per verticil; average distance between verticils about 34.0 mm, greater proximally and less distally; about 15 verticils per plant; about 200 to 350 flowers per panicle;

Flowering period: Flowering beginning late spring for about six weeks and repeating if initial inflorescences removed;

Peduncle: Quadrangular; pubescent to glandular; to 40.0 cm long and 8.0 mm across at base;

Peduncle color: Proximal portion nearest RHS N79A and distal portion nearest RHS 146B;

Flower attitude: Mostly horizontal;

Flower longevity: About four days on the plant or as cut flower; self-cleaning, petals not persistent;

Flower fragrance: None detected under present growing conditions;

Flower buds one day prior to anthesis: Obovoid; arcuate dorsally, flat ventrally and flattened slightly laterally; with rounded apex; pubescent; about 16.0 mm long, 8.0 mm tall and 3.0 mm wide;

Bud color: Exposed petals along dorsal arc nearest RHS 71B, ventral nearest RHS 76B and near center nearest RHS 72A; abaxial calyx nearest RHS 137A variably blushed with RHS 187A;

Petals: Bilabiate corolla; upper hood lip and lower lip (labium) with three lobes; glandular abaxial and glabrous adaxial;

Hood (upper) petal: Glandular abaxial, glabrous adaxial; folded along longitudinal axis; apex rounded and emarginate, with 2 mm deep notched apex and base fused with labium in proximal 10.0 mm; about 27.0 mm long, 7.0 mm tall and 3.0 mm across;

Hood color: Adaxial between RHS 76B and RHS 76C; RHS NN155D, abaxial between RHS 77B and RHS 77C;

Labium (lower) petal: Consisting of three lobes, two proximal side lobes and larger center lobe; side lobes glabrous adaxial and abaxial, center lobe glandular abaxial base and glabrous abaxial margins and distally, adaxial glabrous;

*Center lobe*.—Obcordate; cupped; truncate emarginate apex with notch about 1.0 mm deep; margin crenulate; size about 23.0 mm long (including fuse base) extending 13 mm beyond fusion point; natural width 10.0 mm and when spread to 15.0 mm.

*Center lobe color*.—Adaxial base between RHS N81B and RHS N81C; abaxial nearest RHS N82D near center and near margin nearest RHS N82D.

*Fused corolla color*.—Adaxial base nearest RHS NN155D and toward fusion nearest RHS 67C, abaxial nearest RHS 76B.

*Side lobes*.—Lanceolate; apices acute; base fused to corolla tube; slightly revolute; size about 5.0 mm long from fusion and 2.0 mm wide.

*Side lobes color*.—Nearest RHS N80B adaxial and abaxial.

Androecium: Two; fused with labium, arcuate along inside upper hood petal except when triggered by pollinator;

*Filament*.—Glabrous, fused about 10.0 mm from base of labium petal; arcuate around inside of hood petal; about 21.0 mm long and 0.5 mm diameter with a 3.0 mm long trip by 1.0 mm across mechanism longitudinally folded at base; color of filament between RHS NN155D near base and transitioning to nearest RHS 72B in distal 4 mm; color of trip mechanism between RHS N79C near center and perimeter nearest RHS 76D.

*Anther*.—Glabrous; oblong ellipsoidal; dorsifixed; longitudinal; about 2.0 mm long and 1.0 mm diameter; color nearest RHS N187A.

*Pollen*.—Abundant; less than 0.1 mm circumference; color nearest RHS 12A.

Gynoecium: One, arcuate around inside of hood petal;

*Style*.—Exserted; about 26.0 mm long and 0.5 mm diameter; color nearest RHS NN155D at base, transitioning distally to nearest RHS N79C.

*Stigma*.—Bifurcate and curved in the terminal 2.0 mm; about 0.3 mm diameter; apex acute; color between RHS N186C and RHS N186D.

*Ovary*.—Superior; up to four-seeded; color between RHS 160D and RHS 146D.

Fruit: Nutlet, one to four per flower; globose; about 1.5 mm diameter; color nearest RHS 200A;

Calyx: Campanulate; fused in basal 7.5 mm; tube about 8.0 mm long and 8.0 mm tall at mouth and 4.5 mm wide; lower set bifurcate in distal 0.5 mm; upper set of trifurcate slightly folded in middle in distal 0.5 mm; glandular abaxial and glabrous adaxial;

Sepals: Five, three upper and two lower; linear; acute apex; 8.0 mm long, 2.5 mm across at fusion and fused in basal 7.5 mm;

Sepal color: Adaxial proximal 3 mm nearest RHS 145D with veins nearest RHS 137C, distal portion nearest RHS 137C; abaxial nearest RHS 137A distally, with veins of nearest RHS NN137A blushed with RHS 187A;

Bracts: Each verticil subtended by two opposite deltoid bracts; apex narrowly acute; base sessile, truncate, clasping; margin crenate; glabrous adaxial and pubescent abaxial; bract size up to 18.0 mm long and 13.0 mm wide, decreasing distally;

Bract color: Variable with light intensity, in lower light adaxial surfaces between RHS 137A and RHS NN37A with midrib nearest RHS 145D, abaxial nearest RHS NN137C with midrib of nearest RHS 145D; color in distal portion of peduncle with more intense light exposure between RHS 137A and RHS NN137A with moderate blush of nearest RHS 187A on both surfaces;

Pedicels: Cylindrical; puberulent to glandular; about 2.0 to 3.0 mm long and 1.0 mm diameter; curving outwardly;

Pedicel color: Nearest RHS 145A in proximal portion of peduncle and RHS 187A distally;

Culture: Plants of *Salvia* 'Moulin Rouge' perform best with adequate moisture and good drainage and are hardy from USDA zone 3 to 8.

Disease and pest resistance: Resistant to diseases and pests beyond that common to *Salvia* has not been noted.

It is claimed:

1. The new and distinct perennial *Salvia* plant named 'Moulin Rouge' as herein described and illustrated.

* * * * *